United States Patent [19]

Sugiyama

[11] Patent Number: 5,210,303

[45] Date of Patent: May 11, 1993

[54] PROCESS FOR PRODUCING BENZYLAMINES

[75] Inventor: Tatsuo Sugiyama, Shizuoka, Japan

[73] Assignee: Ihara Chemical Industry Co., Ltd., Tokyo, Japan

[21] Appl. No.: 686,932

[22] Filed: Apr. 18, 1991

[30] Foreign Application Priority Data

Apr. 20, 1990 [JP] Japan .................................. 2-103160

[51] Int. Cl.$^5$ .......................................... C07C 209/06
[52] U.S. Cl. ................................... 564/407; 564/405; 564/406; 564/386
[58] Field of Search ................ 564/407, 405, 404, 386

[56] References Cited

U.S. PATENT DOCUMENTS 2,987,548  6/1961  Magee .................................. 564/386

OTHER PUBLICATIONS

Vassilev et al., Comptes rendus de l'academic bulgare des Sciences, Tome 28, No. 7, (1975).
Merck Index, 1054, 10th Edition, 1983.
Patent Abstracts of Japan, Unexamined Applications, C Field, vol. 12, No. 248, Jul. 13, 1988 The Patent Office Japanese Government p. 6 C 511 *Kokai-No. 63-35 546 (Japan Carlit Co Ltd)*.
Patent Abstracts of Japan, unexamined applications, C Field, vol. 11, No. 357, Nov. 20, 1987 The Patent Office Japanese Government p. 95 C 458 *Kokai-No. 62-129 257 (Daicel Chem Ind Ltd)*.

*Primary Examiner*—Glennon H. Hollrah
*Assistant Examiner*—Shailendra Kumar
*Attorney, Agent, or Firm*—Oblon, Spivak, McClelland, Maier & Neustadt

[57] ABSTRACT

A process for producing a benzylamine which comprises reacting a benzyl halide with an aqueous ammonia solution in the presence of an aromatic aldehyde represented by the formula:

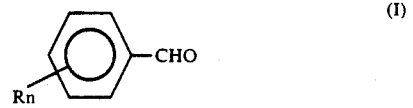

(I)

wherein R represents a hydrogen atom, a halogen atom or a lower alkyl group, and n is 1 or 2, separating an oily substance from the reaction mixture, and treating the oily substance with a mineral acid.

9 Claims, No Drawings

PROCESS FOR PRODUCING BENZYLAMINES

The present invention relates to a process for producing benzylamines from benzyl halides and ammonia in good yield with less production of by-products.

Benzylamines have been widely used as intermediates for the production of pharmaceuticals, agricultural chemicals, dyestuffs, synthetic resins, etc., or as absorbents for carbon dioxide.

As a method for producing benzylamines, there have been known, for example, a method wherein a benzyl halide and an aqueous ammonia solution are reacted (U.S. Pat. Nos. 2,608,584 and 2,987,548), a method wherein a benzyl halide and liquid ammonia are reacted (Japanese Patent Publication No. 6256/1957), and a method wherein phenylnitromethane or nitrobenzil is reduced. Among them, the method wherein a benzyl halide and ammonia are reacted, is considered to be most advantageous from the industrial viewpoint, since the starting material is readily available and no special equipment is needed.

However, when the benzyl halide and aqueous ammonia solution are reacted, the benzylamine is accompanied with by-products such as dibenzylamine. Thus, this process has a drawback that it is necessary to use ammonia in a large amount of not less than 20 moles per mole of the benzyl halide for obtaining the benzylamine in good yield.

It is an object of the present invention to inhibit the production of by-products in a method for producing a benzylamine from a benzyl halide and an aqueous ammonia solution and thereby to obtain a benzylamine in good yield.

The present inventors have conducted expensive researches to develop a process for inhibiting the production of the by-products in preparing the benzylamine and, as a result, have found that the object can be accomplished by conducting the reaction in the presence of an aromatic aldehyde in the reaction system. The present invention has been accomplished on the basis of this discovery.

The present invention provides a process for producing a benzylamine which comprises reacting a benzyl halide with an aqueous ammonia solution in the presence of an aromatic aldehyde represented by the formula:

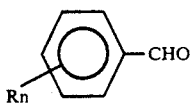
(I)

wherein R represents a hydrogen atom, a halogen atom or a lower alkyl group, and n is 1 or 2, separating an oily substance from the reaction mixture, and treating the oily substance with a mineral acid.

In the present invention, a benzyl halide is used as a starting material. The benzyl halide includes, for example, substituted benzyl halides whose benzene nucleus is substituted with 1 to 2 halogen atoms or low alkyl groups, such as 2-chlorobenzyl chloride, 3-chlorobenzyl chloride, 4-chlorobenzyl chloride, 2-fluorobenzyl chloride, 4-fluorobenzyl chloride, 2,4-dichlorobenzyl chloride, 3,4-dichlorobenzyl chloride, 2,6-dichlorobenzyl chloride, 4-methylbenzyl chloride, 4-ethylbenzyl chloride, 2,4-dimethylbenzyl chloride and α,α'-dichloroxylene, and corresponding bromides and fluorides.

In the process of the present invention, it is necessary to react the benzyl halide and the aqueous ammonia solution in the presence of the aromatic aldehyde represented by the formula (I). The aromatic aldehyde acts as a side reaction inhibitor for the above reaction. The aromatic aldehyde includes, for example, benzaldehyde, 2-chlorobenzaldehyde, 4-chlorobenzaldehyde, 4-fluorobenzaldehyde, 3-chlorobenzaldehyde, 2,4-dichlorobenzaldehyde, 4-methylbenzylaldehyde, 4-ethylbenzylaldehyde and 2,4-dimethylbenzaldehyde.

The aromatic aldehyde is usually used in the range of not less than 1 mole, preferably from 1 to 2 moles, per mole of the benzyl halide used as a starting material.

As an aqueous ammonia solution used for aminating the benzyl halide to the corresponding benzylamine, it is advantageous to use an aqueous ammonia solution prepared by saturating water with ammonia gas at a reaction temperature. The aqueous ammonia solution is used in the ratio based on the ammonia concentration of not less than 2 moles, preferably from 4 to 10 moles, per mole of the benzyl halide. In this case, the reaction rate becomes higher as the amount of ammonia becomes larger.

In the process of the present invention, if desired, there may be used in combination auxiliaries conventionally used for the reaction between the benzyl halide and ammonia, for example, nonaqueous inert organic solvents such as benzene, toluene, xylene, chlorobenzene, dichlorobenzene and diethyl ether, and catalysts such as quaternary ammonium salts.

Now, specific embodiments in practicing adequately the process of the present invention will be described. At first, the benzyl halide, aromatic aldehyde represented by the formula (I) and aqueous ammonia solution which are starting materials, are mixed and reacted in the predetermined proportions. The reaction temperature is usually not less than 30° C., preferably from 50° to 90° C. The reaction time, which depends on the type of starting materials used, reaction temperature, catalysts, etc., is usually from about 1 to 10 hours. After completion of the reaction, the reaction mixture is separated into an aqueous phase and an oil phase by leaving it to stand. Only the oil phase is collected and then treated with a mineral acid. As the mineral acid, nitric acid, phosphoric acid and other inorganic acids can be used, but hydrochloric acid and sulfuric acid are advantageous in view of easiness in handling. The mineral acid is preferably used in the form of an aqueous solution at a concentration of from 1 to 15%, taking into consideration the subsequent operation.

The amount of the mineral acid is usually within the range of not less than 1 mol, preferably from 1 to 2 mols, per mol of the benzyl halide used as a starting material. The treatment with the mineral acid may be conducted at room temperature, but may be conducted at an elevated temperature, or may be conducted under reflux.

The treatment with the mineral acid can be conducted, if desired, in the presence of a nonaqueous inert organic solvent such as benzene, toluene, xylene, chlorobenzene, dichlorobenzene or diethyl ether.

The reaction mixture obtained by the mineral acid treatment is separated into an aqueous phase and an oil phase by leaving it to stand. The aqueous phase contains a benzylamine in the form of a mineral acid salt, and the oil phase contains a regenerated benzaldehyde. After the separation of the aqueous phase, when the oil phase is neutralized with an alkali, the benzylamine as the desired product is liberated. The alkali used in this case may preferably be a hydroxide of an alkali metal or an alkaline earth metal such as sodium hydroxide or potassium hydroxide. The alkali is used in an amount of not less than 1 mol, preferably not less than 1.1 mols, per mol of the mineral acid used for the mineral acid treatment.

The neutralization may be, if desired, conducted in the presence of a nonaqueous inert organic solvent such as benzene, toluene, xylene, chlorobenzene, dichlorobenzene or diethyl ether.

By distilling the neutralized oil phase under a reduced pressure, a benzylamine can be obtained in good yield.

On the other hand, the oil phase separated from the aqueous phase in the above-mentioned mineral acid treatment contains a benzaldehyde, and thus the benzaldehyde can be reused by using the oil phase as such, or after the recovery from the oil phase.

The oil phase after the mineral acid treatment sometimes contains an unreacted benzyl chloride as well as the benzaldehyde. When such an oil phase is reused, the amount of the unreacted benzyl chloride can be reduced from the amount of the benzyl chloride as a starting material necessary at the start of the recycled operation.

The recovery of the benzaldehyde from the oil phase may be conducted by a conventional method such as evaporation or solvent extraction. The benzaldehyde thus recovered can be applied to the reaction step by mixing it with a fresh benzaldehyde supplemented in an amount corresponding to the consumed benzaldehyde. The excess amount of the aqueous ammonia solution used for the reaction can be reused by adjusting it to a predetermined concentration by blowing ammonia gas thereinto or adding an aqueous ammonia solution of high concentration.

In the process for producing a benzylamine by reacting a benzyl halide and an aqueous ammonia solution, the yield of not less than 50% has never been realized by the inevitable by-production of a secondary amine and a tertiary amine. The present invention provides such advantages that the formation of by-products can be inhibited, the yield of not less than 70% can be realized, and also the product of very high quality can be obtained by a quite simple method wherein the reaction is carried out in the presence of the aromatic aldehyde as a side reaction inhibiter.

In addition, the aromatic aldehyde used as a side reaction inhibiter can be recovered substantially completely, and repeatedly reused only by supplementing a little consumed amount. Thus, there is substantially no adverse effect to the cost of the product. Accordingly, the process of the present invention is preferred as a process for producing the benzylamine on an industrial scale.

Further, when the conventional method is conducted at a temperature of not less than 35° C., considerable amount of a di-substituted product is produced, thereby the conventional method must be conducted at a low temperature and the reaction time inevitably becomes longer. However, the present invention provides an advantage that no by-product is produced if the reaction temperature is elevated to 40° C. or higher and thus the reaction time can be shortened.

Now, the present invention will be described in further detail with reference to Examples. However, it should be understood that the present invention is by no means restricted to such specific Examples.

EXAMPLE 1

Into a 300 ml four-necked flask equipped with a stirrer, a thermometer and a reflux condenser, 195 g of a 7% aqueous ammonia solution (0.80 mol in terms of $NH_3$) was charged and, while maintaining the internal temperature of the flask at 70° to 75° C., 16.1 g (0.10 mol) of 2-chlorobenzyl chloride and 28.1 g (0.20 mol) of 2-chlorobenzaldehyde were added thereinto simultaneously, followed by a reaction for 4 hours. After completion of the reaction, the flask was left to stand for a short time, and a separated oil phase was collected.

Separately, into a 300 ml four-necked flask equipped with a stirrer, a thermometer and a reflux condenser, 100 g of chlorobenzene and 109.5 g of a 10% hydrochloric acid (0.30 mol in terms of HCl) were charged. The oil phase collected as mentioned above was added thereto, and the mixture was stirred at room temperature for 30 minutes. A reaction mixture separated into two phases was thus obtained. An aqueous phase was collected from the reaction mixture and mixed with 100 g of chlorobenzene, 27.5 g (0.33 mol) of a 48% sodium hydroxide aqueous solution and 104.5 g of water, and stirred. After completion of the reaction, an oil phase was collected by separation from the reaction mixture, dried, and distilled under a reduced pressure of 18 mmHg to obtain 9.3 g of 2-chlorobenzylamine as a fraction having a boiling point of 106° C., which amounts to 80% as a yield based on 2-chlorobenzyl chloride.

COMPARATIVE EXAMPLE

The operation was conducted in the same manner as in Example 1 except that 2-chlorobenzaldehyde was not added and, as a result, 1.53 g of 2-chlorobenzylamine was obtained which amounts to 11.6% as a yield based on 2-chlorobenzyl chloride.

As apparent from this Comparative Example, when 2-chlorobenzaldehyde is not used, the yield is considerably low.

EXAMPLE 2

Into a 1 l four-necked flask equipped with a stirrer, a thermometer and a reflux condenser, 728 g of a 7% aqueous ammonium solution (3.0 mols in terms of $NH_3$) and, while maintaining the internal temperature of the flask at 70° to 75° C., 80.5 g (0.50 mol) of 3-chlorobenzyl chloride and 53 g (0.5 mol) of benzaldehyde and 0.1 g of tetrabutylammonium bromide were admixed thereinto, followed by a reaction for 4 hours. After completion of the reaction, the reaction mixture was left to stand for a short time, and a separated oil phase was collected.

Separately, into a 1 l four-necked flask, 548 g of a 5% hydrochloric acid (0.75 mol in terms of HCl) and 300 g of chlorobenzene were charged. The oil phase separated as mentioned above was added thereto, and stirred at 80° C. for 30 minutes. Then, a chlorobenzene phase was collected by separation, mixed with 150 g of fresh chlorobenzene and 69 g (0.83 mol) of a 48% sodium hydroxide aqueous solution, and reacted. An oil phase formed after the reaction was collected by separation, washed and dried according to a conventional method, and distilled under a reduced pressure of 20 Torr to obtain 49.0 g (73% based on 3-chlorobenzyl chloride) of 3-chlorobenzylamine as a fraction of 113° C.

EXAMPLE 3

Into a 300 ml four-necked flask equipped with a stirrer, a thermometer and a reflux condenser, 195 g of a 7% aqueous ammonia solution (0.80 mol in terms of $NH_3$) was charged and, while maintaining the internal temperature of the flask at 70° to 75° C., 14.5 g (0.10 mol) of 4-fluorobenzyl chloride and 10.6 g (0.10 mol) of benzaldehyde were added thereto simultaneously, followed by a reaction for 4 hours. After completion of the reaction, the reaction mixture was left to stand, and a separated oil phase was collected by separation.

Separately, into a 300 ml four-necked flask, 100 g of a 5% hydrochloric acid (0.15 mol in terms of HCl) was charged. The oil phase collected as mentioned above was added thereinto, and stirred at room temperature for 30 minutes. Then, the reaction mixture was left to stand for phase separation, and an aqueous phase was collected and extracted with 100 m of diethyl ether. The aqueous phase thus treated was added with 13.8 g of a 48% sodium hydroxide aqueous solution (0.165 mol in terms of NaOH) and 100 ml of diethyl ether, and stirred for 1 hour. An oil phase was separated, and an aqueous phase was extracted again with diethyl ether. The solutions extracted with diethyl ether were combined and distilled to obtain 8.86 g of 4-fluorobenzylamine as a fraction having a boiling point of 95° C./35 mmHg, which amounts to 71% as a yield based on 4-fluorobenzyl chloride.

EXAMPLE 4

Into a 500 ml four-necked flask equipped with a stirrer, a thermometer and a reflux condenser, 181 g of a 15% aqueous ammonia solution (1.60 mols in terms of $NH_3$) was charged and, while maintaining at 50° C., 28.1 g (0.20 mol) of 4-methylbenzyl chloride and 42.4 g (0.40 mol) of benzaldehyde were charged thereinto, followed by a reaction for 24 hours. After completion of the reaction, the reaction mixture was left to stand for phase separation, and an oil phase was collected by separation.

Into another 500 ml four-necked flask, 220 g of 5% hydrochloric acid (0.30 mol in terms of HCl) was charged. The above-mentioned oil phase was added thereto, followed by stirring at 40° C. for 30 minutes. After completion of the reaction, an oil phase was removed from the reaction mixture, and an aqueous phase was extracted with 100 ml of diethyl ether and washed. The aqueous phase was added with 27.5 g of a 48% sodium hydroxide aqueous solution (0.33 mol in terms of NaOH) and 100 ml of diethyl ether were added thereto, and stirred. An oil phase was separated from the product thus treated, and an aqueous phase was extracted again with 100 ml of diethyl ether. The extract was combined to the oil phase, and the combined oil phase was dried and distilled under a reduced pressure of 20 Torr to obtain 15.3 g of 4-methylbenzylamine as a fraction having a boiling point of 94° C., which amounts to 70% as a yield based on 4-methylbenzyl chloride.

EXAMPLE 5

Into a 500 ml four-necked flask equipped with a stirrer, a thermometer and a reflux condenser, 392 g of a 7% aqueous ammonia solution (1.6 mols in terms of $NH_3$) was charged and, while maintaining the internal temperature of the flask at 70° to 75° C., 25.3 g (0.2 mol) of benzyl chloride and 42.4 g (0.4 mol) of benzaldehyde were added thereto simultaneously, followed by a reaction for 3 hours. After completion of the reaction, the reaction mixture was left to stand for a short time, and a separated oil phase was collected.

Separately, into a 500 ml four-necked flask equipped with a stirrer, a thermometer and a reflux condenser, 200 g of diethyl ether and 219 g of 5% hydrochloric acid (0.3 mol in terms of HCl) were charged. The oil phase separated as mentioned above was added thereto, and stirred at room temperature for 30 minutes. Thus, a reaction mixture separated into two phases was obtained. An aqueous phase was collected by separation and mixed with 200 g of diethyl ether and 27.5 g (0.33 mol) of a 48% sodium hydroxide aqueous solution, followed by stirring. After completion of the reaction, an oil phase was collected by separation from the reaction mixture, and then dried, and distilled under reduced pressure of 10 mmHg to obtain 16.8 g of benzylamine as a fraction having a boiling point of 66° C., which amounts to 82.6% as a yield based on benzyl chloride.

EXAMPLE 6

Into a 2l four-necked flask equipped with a stirrer, a thermometer and a reflux condenser, 1,456 g of a 7% aqueous ammonia solution (6 mols in terms of $NH_3$) was charged and, while maintaining at 70° to 75° C., 161 g (1.0 mol) of 2-chlorobenzyl chloride and 106 g (1.0 mol) of benzaldehyde were added thereinto, followed by a reaction for 4 hours. After completion of the reaction, the reaction mixture was left to stand for phase separation, and an oil phase was collected by separation.

Into another 2 l four-necked flask, 1,095 g of 5% hydrochloric acid (1.50 mols in terms of HCl) was charged. The above-mentioned oil phase was added thereto, and stirred for 30 minutes as such.

Then, the mixture was separated into an oil phase (A) and an aqueous phase (B), and the aqueous phase was extracted with 600 g of monochlorobenzene and washed. Next, the aqueous phase was added with a 48% sodium hydroxide aqueous solution (1.65 mols in terms of NaOH) and 300 g of monochlorobenzene, and stirred, then and an oil phase was collected by separation. The collected oil phase was washed, dried and distilled under a reduced pressure to obtain 88.8 g of 2-chlorobenzylamine, which amounts to 62.8% as a yield based on 2-chlorobenzyl chloride.

The aqueous phase (which contained an excess amount of ammonia) collected by separation from the first reaction mixture was added with 125 g of a 28% aqueous ammonia solution, and further added with the oil phase (banzaldehyde containing 0.15 mol of the unreacted 2-chlorobenzyl chloride) separated from the above-mentioned product, treated with hydrochloric acid, 136.9 g (0.85 mol) of 2-chlorobenzyl chloride and 15.7 g (0.15 mol) of benzaldehyde, followed by a reaction at 70° to 75° C. for 4 hours.

The reaction mixture was treated in the same manner as mentioned above to obtain 103.0 g of 2-chlorobenzylamine, which amounts to 85.6% as a yield based on 2-chlorobenzyl chloride.

This operation was further repeated twice and the result shown below was obtained.

|  | Number of operation | | | |
| --- | --- | --- | --- | --- |
|  | 1st | 2nd | 3rd | 4th |
| Yield of 2-chloro- | 88.8 | 103.0 | 111.1 | 111.6 |

| -continued | Number of operation | | | |
|---|---|---|---|---|
| | 1st | 2nd | 3rd | 4th |
| benzylamine (g) Yield based on 2-chlorobenzyl chloride (%) | 62.8 | 85.6 | 92.4 | 92.8 |

As apparent from the above results, by recovering and reusing the benzaldehyde used as the side reaction inhibitor, the yield of the desired 2-chlorobenzylamine based on the chloride as a starting material is considerably increased.

EXAMPLE 7

Into a 500 ml four-necked flask equipped with a stirrer, a thermometer and a reflux condenser, 392 g of a 7% aqueous ammonia solution (1.6 mols in terms of $NH_3$) was charged and, while maintaining the internal temperature of the flask at 70° to 75° C., 25.3 g (0.20 mol) of benzyl chloride and 53.6 g (0.40 mol) of 4-ethylbenzaldehyde were added thereinto at the same time, followed by a reaction for 3 hours. After completion of the reaction, the reaction mixture was left to stand for a short time, and a separated oil phase was collected by separation.

Separately, into a 500 ml four-necked flask equipped with a stirrer, a thermometer and a reflux condenser, 200 g of diethyl ether and 219 g of a 5% hydrochloric acid (0.30 mol in terms of HCl) were charged. The oil phase separated as mentioned above was added thereto, followed by stirring at room temperature for 30 minutes. Thus, a reaction mixture separated into two phases was obtained. An aqueous phase was collected by separation from the reaction mixture, mixed with 200 g of diethyl ether and 27.5 g (0.33 mol) of a 48% sodium hydroxide aqueous solution, and stirred. After completion of the reaction, an oil phase was collected by separation from the reaction mixture, dried, distilled under a reduced pressure of 10 mmHg to obtain 15.5 g of benzylamine as a fraction having a boiling point of 66° C., which amounts to 75.4% as a yield based on benzyl chloride.

I claim:

1. A process for producing a benzylamine which comprises reacting a benzyl halide with an ammonia solution in the presence of an aromatic aldehyde represented by the formula:

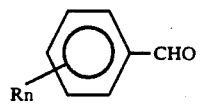

(I)

wherein R represents a hydrogen atom, a halogen atom or a lower alkyl group, and n is 1 or 2, separating an oily substance from the reaction mixture, and treating the oily substance with a mineral acid, wherein the aromatic aldehyde is in an amount of not less than 1 mol per mol of the benzyl halide and the ammonia in the aqueous ammonia solution is in an amount of 2 to 10 moles per mole of the benzyl halide.

2. The process according to claim 1, wherein the aromatic aldehyde is at least one member selected from the group consisting of benzaldehyde, 2-chlorobenzaldehyde, 4-chlorobenzaldehyde, 4-fluorobenzaldehyde, 3-chlorobenzaldehyde, 2,4-dichlorobenzaldehyde, 4-methylbenzylaldehyde, 4-ethylbenzylaldehyde and 2,4-dimethylbenzaldehyde.

3. The process according to claim 1, wherein the aromatic aldehyde is used in an amount of from 1 to 2 mols per mol of the benzyl halide.

4. The process according to claim 1, wherein the aqueous ammonia solution is used in an amount of 4 to 10 moles per mole of the benzyl halide.

5. The process according to claim 1, wherein the reaction is conducted at a temperature of 30° C. or higher.

6. The process according to claim 1, wherein the reaction is conducted at a temperature of from 50° to 90° C.

7. The process according to claim 1, wherein the mineral acid is at least one member selected from the group consisting of nitric acid, phosphoric acid, hydrochloric acid and sulfuric acid.

8. The process according to claim 1, wherein the mineral acid is used in an amount of not less than 1 mole per mole of the benzyl halide.

9. The process according to claim 1, wherein the mineral acid is used in an amount of 1 to 2 moles per mole of the benzyl halide.

* * * * *